United States Patent
Chapaton et al.

(10) Patent No.: US 10,343,496 B2
(45) Date of Patent: Jul. 9, 2019

(54) ANTIMICROBIAL UV-C TREATMENT FOR AUTOMOTIVE HVAC SYSTEMS

(71) Applicant: GM Global Technology Operations LLC, Detroit, MI (US)

(72) Inventors: Thomas J. Chapaton, Sterling Heights, MI (US); Michael J. Llerandi, Miami, FL (US); Keith V. Huguley, West Bloomfield, MI (US); Mark A. Gordon, Oxford, MI (US)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 129 days.

(21) Appl. No.: 14/876,945

(22) Filed: Oct. 7, 2015

(65) Prior Publication Data

US 2017/0100989 A1   Apr. 13, 2017

(51) Int. Cl.
| | | |
|---|---|---|
| *B60H 3/00* | (2006.01) | |
| *C02F 1/32* | (2006.01) | |
| *A61L 2/10* | (2006.01) | |
| *A61L 9/20* | (2006.01) | |
| *B60H 1/32* | (2006.01) | |
| *C02F 103/02* | (2006.01) | |
| *F25D 27/00* | (2006.01) | |

(52) U.S. Cl.
CPC .............. *B60H 3/0085* (2013.01); *A61L 2/10* (2013.01); *A61L 9/20* (2013.01); *C02F 1/325* (2013.01); *A61L 2209/16* (2013.01); *B60H 1/3227* (2013.01); *B60H 1/3233* (2013.01); *B60H 3/0092* (2013.01); *C02F 2103/023* (2013.01); *C02F 2201/3222* (2013.01); *C02F 2201/3224* (2013.01); *C02F 2201/3227* (2013.01); *C02F 2201/3228* (2013.01); *F25D 27/00* (2013.01); *F25D 2317/0417* (2013.01)

(58) Field of Classification Search
CPC ............. F25D 27/00; F25D 2317/0417; B60H 1/3233; B60H 3/0085; B60H 3/0092
See application file for complete search history.

(56) References Cited

U.S. PATENT DOCUMENTS

| | | | | |
|---|---|---|---|---|
| 5,311,407 A | * | 5/1994 | Lumbard | H01L 23/49534 174/536 |
| 6,422,301 B1 | * | 7/2002 | Scoccia | B60H 1/3233 165/42 |
| 2003/0019222 A1 | * | 1/2003 | Takahashi | F25D 17/042 62/131 |
| 2004/0065107 A1 | * | 4/2004 | Bas | B60H 3/0085 62/303 |
| 2007/0144351 A1 | * | 6/2007 | Taira | A61L 9/205 96/223 |
| 2007/0175063 A1 | * | 8/2007 | Morgan | F26B 21/086 34/467 |
| 2013/0059047 A1 | * | 3/2013 | Arrigo | A23B 7/148 426/320 |
| 2013/0167573 A1 | * | 7/2013 | Almblad | F25C 1/00 62/340 |
| 2015/0165079 A1 | * | 6/2015 | Shur | A61L 2/10 250/455.11 |

* cited by examiner

*Primary Examiner* — David J Teitelbaum

(57) ABSTRACT

Methods and systems for reducing microbial contamination and growth in an automotive HVAC system by irradiating one or more air contacting surfaces of the HVAC system with antimicrobial UV-C light.

19 Claims, 2 Drawing Sheets

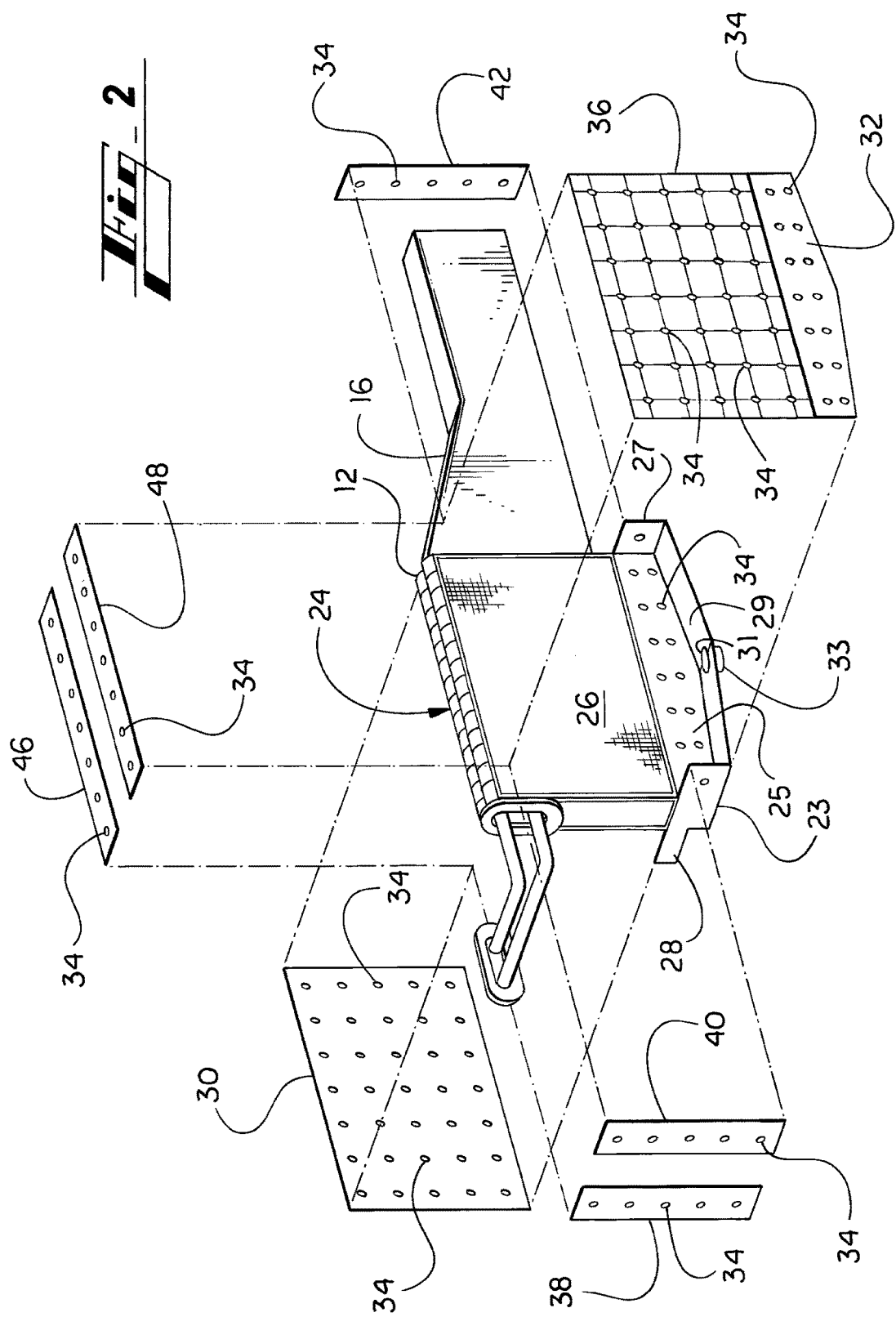

ANTIMICROBIAL UV-C TREATMENT FOR AUTOMOTIVE HVAC SYSTEMS

BACKGROUND

Automotive heating, ventilation, and air conditioning (HVAC) systems generally incorporate a large, hollow housing behind the instrument panel, which contains a cold evaporator core and hot heater core, as well as various valves for directing air flow through them and ultimately out into the passenger compartment.

During air conditioning operation, refrigerant is circulated through the evaporator core to cool and dehumidify air before it is directed to the passenger compartment. Moisture condenses within the air passages of the evaporator core and in other portions of the HVAC system. This collected moisture, in some instances, promotes the growth of microorganisms. If the growth is excessive, it may produce an unpleasant odor or otherwise deleteriously affect passenger comfort.

SUMMARY

There is a need for a method to minimize surface microbial growth, waterborne microorganisms, biofilms, airborne microorganisms, and bioaerosols in automotive HVAC systems. Strategic placement of ultraviolet C (UV-C) emitting devices(semiconductors) within the automotive HVAC system can kill microorganisms and minimize material surface microbial growth, waterborne microorganisms, biofilms, airborne microorganisms, and bioaerosols. This minimizes the offensive odors caused by microorganisms and their corresponding metabolized products. Minimizing microbial growth may offer occupants health benefits by enhancing overall vehicle interior air quality.

An example of an automotive HVAC system includes an evaporator core to cool and dehumidify moisture-containing air caused to flow through the HVAC system and into a passenger compartment. When the liquid refrigerant reaches the evaporator its pressure has been reduced, dissipating its heat content and making it much cooler than the blower air flowing around it. This causes the refrigerant to absorb heat from the warm air and reach its low boiling point rapidly. The refrigerant then vaporizes, absorbing the maximum amount of heat. This heat is then carried by the refrigerant from the evaporator as a low-pressure gas through a hose or line to the low side of the compressor, where the whole refrigeration cycle is repeated. The evaporator core includes air-contacting surfaces upon which water condenses after the moisture-containing air flows thereover and is cooled and dehumidified.

The HVAC system further includes air-communicating conduits operatively connected to at least one of the evaporator core and the passenger compartment. A sump assembly includes sump side walls, sump floor, and a sump drain, all having air-contacting surfaces. The sump assembly receives the condensed water from the evaporator core. An exterior drain assembly is operatively connected to the sump assembly via the sump drain.

All of the automotive HVAC components upon which water condenses or otherwise contacts are susceptible to microbial growth. In one aspect the invention is exposing one or more of these water contacting areas to antimicrobial UV-C light.

In another aspect the invention is exposing one or more air contacting surfaces of an automotive HVAC system to antimicrobial UV-C light.

In various aspects, the invention is methods of preventing or reducing microbial contamination and growth inside an automotive HVAC system by contacting the automotive HVAC system internal components with antimicrobial UV-C light.

In one embodiment, UV emitting devices are placed on or in the HVAC system so that they illuminate one or more of the evaporator core, evaporator coil, the core frame, any air-contacting surfaces, any water-contacting surfaces, the air-communicating conduits, or the sump assembly. An evaporator coil is a component in the HVAC system and the corresponding tubes and fins are sub-components. One or more UV emitting devices are placed so that they expose one or more of these areas to antimicrobial UV irradiation.

Other aspects and features of the present invention will be in part apparent and in part pointed out hereinafter.

BRIEF DESCRIPTION OF THE DRAWINGS

Features and advantages of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

FIG. 2 is an exploded view illustrating one embodiment of LED placement in an automotive HVAC system.

Figure 1:
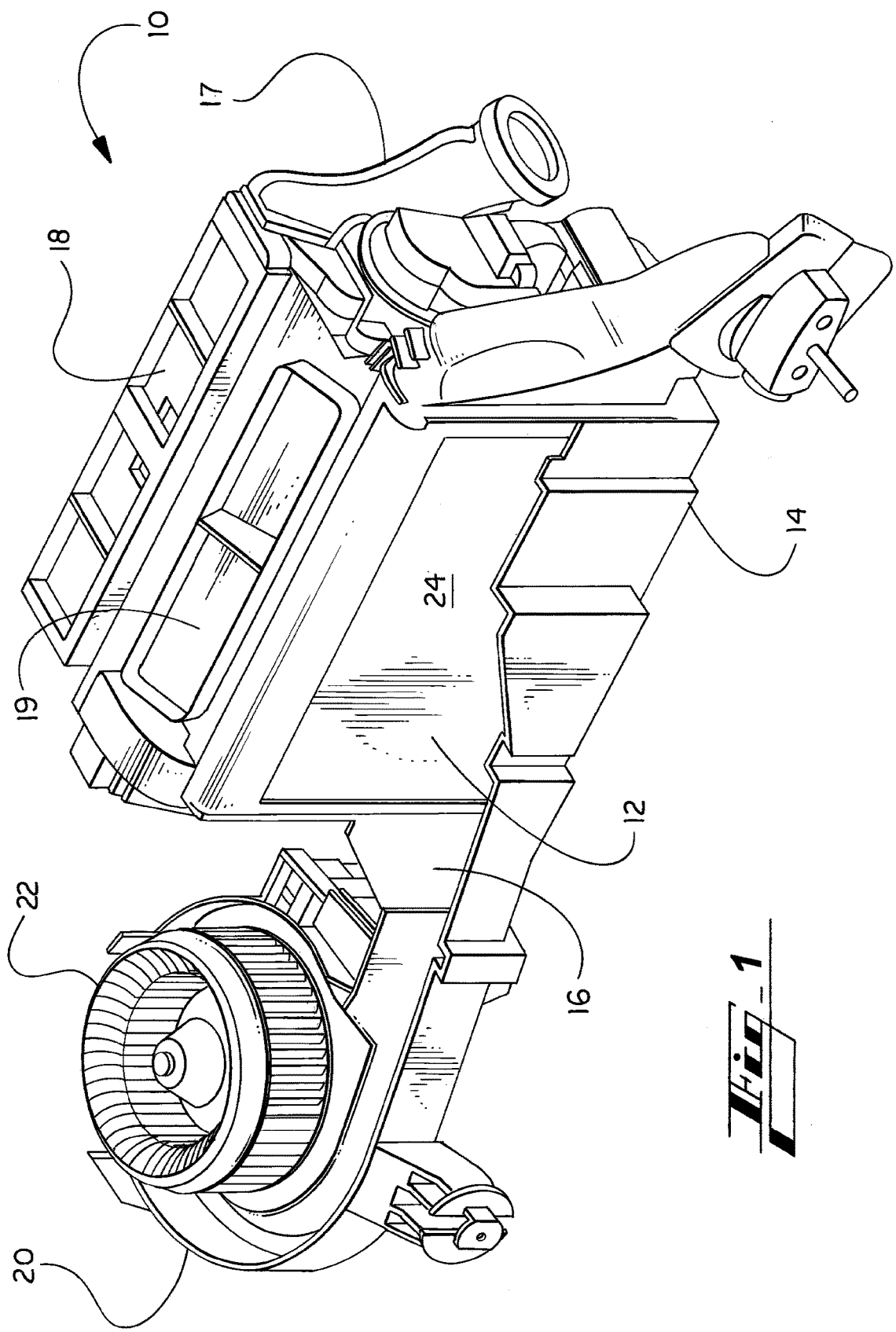
FIG. 1 is a semi-schematic, cutaway, perspective view of an automotive HVAC unit.

The figures are not necessarily to scale and some features may be exaggerated or minimized, such as to show details of particular components. In some instances, well-known components, systems, materials or methods have not been described in detail in order to avoid obscuring the present disclosure.

Specific structural and functional details disclosed herein are not to be interpreted as limiting, but merely as a basis for the claims and as a representative basis for teaching one skilled in the art to variously employ the present disclosure.

DETAILED DESCRIPTION

As required, detailed embodiments of the present disclosure are disclosed herein. The disclosed embodiments are merely examples that may be embodied in various and alternative forms, and combinations thereof. As used herein, for example, "exemplary" and similar terms, refer expansively to embodiments that serve as an illustration, specimen, model, or pattern.

While the present technology is described primarily herein in connection with automobiles, the technology is not limited to automobiles. The concepts can be used in a wide variety of applications.

The present disclosure provides, by way of various embodiments, systems and methods for reducing contamination and growth of microorganisms in the HVAC system of an automobile. The systems and methods thus reduce the odors caused by such microorganisms and may provide health benefits.

The HVAC system in an automotive vehicle is a difficult place to keep free from odor-causing bacteria, fungi, mold, mildew, and algae. It is difficult to keep HVAC system interior surfaces clean and protected against microbial infiltration. Microbial infiltration may start from the exterior (fresh air mode) or interior (recirculation mode). Microbes may grow and thrive naturally within conditions that exist inside a dark, damp HVAC system, and an untreated system may be susceptible to extensive growth and contamination.

The term "microorganisms" refers to bacteria, fungi, mold, mildew, algae, and viruses. The term "anti-microbial" refers to a composition or an agent that kills microorganisms or inhibits their growth.

Ultraviolet (UV) irradiation is electromagnetic irradiation with a wavelength (100-400 nm) shorter than that of visible light (400-700 nm), but longer than x-rays (<100 nm). UV irradiation is divided into four distinct spectral areas including vacuum UV (100-200 nm), UV-C (200-280 nm), UV-B (280-315 nm), and UV-A (315-400 nm). Within the UV-C spectrum, 250-280 nm is the most lethal wavelength range for microorganisms and is known as the germicidal spectrum, with 265 nm being the peak germicidal wavelength. The intense UV-C photon energy attacks the DNA of a living cell, penetrating the cell membrane, breaking the DNA structure of the microorganism and rendering it harmless by robbing it of the ability to reproduce. UV-C kills or de-activates microorganisms, even if they have become immune to other disinfection methods.

Preferably the UV-C emitting devices used in the HVAC systems according to the invention emit UV-C irradiation in the wavelength range 200-280 nm, most preferably 250-280 nm, even more preferably 265 nm.

UV LEDs offer the advantages of a small size and minimal power consumption. They have a long life, are durable, and are inexpensive. A variety of UV-C light emitting devices can be used. Preferably the UV-C light emitting devices are semiconductors such as light-emitting-diode (LED). Useful LEDs include high power "Phlatlight" photonic lattice LEDs and multi-chip deep-UV LEDs.

The semiconductor light source can be contained in a surface mounted device (SMD) chip, star base chip, chip on board (COB), flip chip (FC), multi-chip, strip set, printed circuit board (PCB), photonic lattice chip, or transistor case package. Examples of surface mounted device chips are SMD-6868, -6565, -6060, -5730, -5630-5050, -3528, -3020, -3014, -2835. Examples of semiconductors with a round base are P5, P6, P7, P8, P10, P12; flip chips include LM131A, LH141A. A useful transistor case package is the TO-3/5/8/18/39/46/52/72

In one preferred embodiment the semiconductor device is one that employs aluminum gallium nitride (AlGaN) or aluminum indium gallium nitride (AlInGaN) multiple quantum wells (MQWs) over sapphire substrates or aluminum nitride (AlN) substrates. More preferably, the device employs aluminum indium gallium nitride (AlInGaN) multiple quantum wells (MQWs) over a patented sapphire substrate (PSS) with backside roughening process as taught, for example in U.S. Pat. No. 9,112,103. The UV-C LED devices are desirably waterproof.

One or more UV-C emitting devices are strategically placed in the HVAC system to irradiate areas of the HVAC system which come into contact with airborne or waterborne microbes. Two or more areas can be irradiated simultaneously or sequentially. Particular areas or components that can be irradiated are the air-contacting surfaces in the evaporator core such as the evaporator coils, area supstream and downstream of the evaporator core, air-communicating conduits, the sump assembly including the interior of the sump assembly walls, the sump floor, the sump drain, the core frame, HVAC system components, and accessories thereof.

To adequately irradiate the desired areas or components, it may be beneficial to mount the UV-C devices within the HVAC system downstream of the evaporator coils, upstream of the coils, on the sump assembly interior walls, above the sump pan, and/or on the walls of the HVAC system. It may be desirably to mount the UV-C devices near both sides of the evaporator core especially for use with deep coil systems and/or complex fin geometry. Enhanced coil illumination may be accomplished by mounting the UV-C devices perpendicular and parallel to the core face. Such placement offers the advantages of adequate lumens, dwell time, and reflection.

In another embodiment, UV light emitting devices are integrated within evaporator coils directly. Examples of suitable devices include fiber optic and light tube materials used within the coil construction.

The device should preferably be placed so that it is grounded via the vehicle chassis/body ground. This ground would also be considered the battery negative (−) ground.

The UV-C semiconductor light source should be mounted onto a heat sink (passive heat exchanger) for adequate heat dissipation into surrounding medium.

Because the HVAC system contains many convoluted and inaccessible surfaces (for example: the evaporator coils complex geometric fin structure) it may be useful to have means whereby the UV-C light source delivers light indirectly to illuminate obstructed areas via fiber optics, light tubes, minors, prisms, and/or reflective surfaces.

Water contained within the core or sump provides additional inherent reflection and refraction to deliver projected UV-C light source to microbial-ridden surfaces. This enhances illumination in multiple areas and obstructed areas, such as complex geometric shapes containing water condensate within the evaporator coil construction.

In another embodiment, the UV light emitting device is used in combination with another antimicrobial treatment such as antimicrobial additives such a biocides, ionic air purification technology, and programmable AC after blow algorithms.

Polymer UV stabilizers and hindered amine light stabilizers are optionally included for protection of any plastic components that are contacted by the UV-C radiation. This can include the sump assembly, evaporator core frame, and any applied polymer coatings such as on the evaporator coils. Accelerated polymer degradation may occur without the presence of UV absorbers and hindered amine light stabilizer (HALS). Any HVAC components containing plastic and which are contacted by the UV-C light should preferably include stabilizers.

In one embodiment, 0.1 to 1% wt % of the UV absorber 2-(4,6-diphenyl-1,3,5-triazin-2-yl)-5-[(hexyl)oxy]-phenol [$C_{27}H_{27}N_3O_2$, CAS# 147315-50-2] is used with 0.5 to 10 wt % titanium dioxide ($TiO_2$, CAS# 1317-70-0) and 0.1 to 1% wt % of bis(2,2,6,6-tetramethyl-4-piperidyl) sebacate ($C_{28}H_{52}N_2O_4$, CAS# 52829-07-9), which is a HALS radical scavenger.

The methods and systems taught herein can include a lock-out which prevents eye and skin exposure to UV light. For example, the system can include a lockout wire harness switch must be switched off before removing a light source from single/multiple point source modules.

The UV-C semiconductor light source can be controlled through the HVAC Control Module. The UV-C semiconductor light source can be turned on during air conditioning operation such as when a request/command for the AC compressor to turn on is requested by the driver through the HVAC control panel on the vehicle's instrument panel.

Further steps to prevent accidental exposure to UV-C light include service instructions to disconnect the battery negative (−) cable in order to disable the electrical system and prevent the UV-C light source from turning on. In addition, UV-C warning labels could be attached to the HVAC case/distribution box.

Referring now to FIG. 1, an automotive heating, ventilation, and air conditioning (HVAC) system is designated generally at 10. The HVAC unit 10 includes an evaporator core 12 to cool and dehumidify moisture-containing air caused to flow through the HVAC unit 10 and into a passenger compartment. The evaporator core 12 includes air-contacting surfaces upon which water condenses after the moisture-containing air flows thereover and is cooled and dehumidified. The HVAC unit 10 further includes a plurality of air-communicating conduits operatively connected to and communicating with the evaporator core 12 and/or the passenger compartment, including but not limited to a plenum assembly, a plenum grid, a plenum drain, upstream evaporator duct 16, floor duct 17, blower housing 20, blower 22, a blower module drain assembly, a filter assembly, a filter frame, face outlet doors 18, defrost outlet doors 19, door frames, and interior module duct work. Sump assembly (not shown in FIG. 1) is behind the evaporator case wall 14 (shown in cutaway view).

As shown in FIG. 1, fresh and/or recirculated humidified warm air moves from the blower 22 via the blower duct 20 and upstream evaporator duct 16 through the evaporator core 12. The upstream surface 24 of evaporator core 12 is shown.

FIG. 2 is an exploded view illustrating one embodiment of LED placement on an HVAC system. Upstream surface 24 of evaporator core 12 is not shown. Downstream surface 26 of evaporator core 12 is shown. A condensate sump assembly 23 located downstream includes sump side walls 25, 27, 28, 32, sump floor 29, and sump drain hole 31. Note that wall 32 is shown exploded away from the assembly 23. The condensate sump assembly 23 is in fluid communication with the air-contacting surfaces. The condensate sump assembly receives condensed water via forced air and gravity. The exterior drain assembly 33 also located downstream is in fluid communication with the condensate sump assembly 23. An exterior drain assembly 33 is operatively connected to the sump drain hole 31 which receives and expels condensed water away from vehicle via gravity.

A plurality of semiconductors 34 are placed on walls around the evaporator core 12 to illuminate the evaporator coil fin surfaces 24, 26 (and the tube surfaces within—not shown), core frame, and the sump assembly 23 interior. A plurality of semiconductors 34 are arranged on wall 30 which is generally parallel with evaporator surface 24. This wall 30 can be the interior of evaporator case wall 14. Semiconductors 34 are also arranged on side walls 38, 40, and 42 and top walls 46, 48, all shown in exploded view. Sump assembly walls 25, 27, 28, 32 also are shown with semiconductors 34 thereon.

A fence 36 having a plurality of LEDs 34 mounted thereon is placed on the downstream side of evaporator core 12 so that the LEDs illuminate the downstream evaporator coil fin surface 26 of evaporator core 12. Fence 36 allows free circulation of dehumidified cool air from the evaporator core 12 into the vehicle cabin via the floor outlet ducts, face outlet ducts, defrost outlet ducts, or other HVAC outlet ducts.

The fence 36 can have a number of designs, important aspects are that it allows free flow of air and provides a surface upon which to mount the desired number and arrangement of semiconductors.

Note that walls 30, 38, 46 may be present in a motor vehicle HVAC system as the evaporator case. In this instance the semiconductors can be mounted to the interior of the evaporator case walls. All of the walls 30, 38, 40, 42, 46, 48, and fence 36 can be made of polymer, polymer coated metallic alloy, metallic alloy or anodized aluminum. The semiconductors can be mounted to the walls through methods known in the art, such as adhesive, welding, etc. The semiconductors are desirably placed in arrays as shown, although any arrangement is possible.

The methods and systems according to examples of the present disclosure provide UV-C light sources that irradiate one or more of the evaporator core, evaporator coil, the core frame, any air-contacting surfaces, any water-contacting surfaces, the air-communicating conduits, or the sump assembly. An evaporator coil is a component in the HVAC system and the corresponding tubes and fins are sub-components.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

In describing and claiming the examples disclosed herein, the singular forms "a", "an", and "the" include plural referents unless the context clearly dictates otherwise.

Many of the benefits and advantages of the present technology are described herein above. The present section restates some of those and references some others. The benefits are provided by way of example, and are not exhaustive of the benefits of the present technology.

It is believed that examples of the present disclosure may advantageously minimize overall (as well as respiratory allergy-causing and pathogenic) microorganisms including bacteria (including odor-causing bacteria), fungi, mold, mildew and algae in a vehicle HVAC system. Examples of the present disclosure may also enhance/improve vehicle interior air quality.

The above-described embodiments are merely exemplary illustrations of implementations set forth for a clear understanding of the principles of the disclosure. Variations, modifications, and combinations may be made to the above-described embodiments without departing from the scope of the claims. All such variations, modifications, and combinations are included herein by the scope of this disclosure and the following claims. All references cited herein are incorporated herein in their entirety.

The invention claimed is:
1. An automotive heating, ventilation and air conditioning (HVAC) system, comprising:
 an evaporator housing comprising an evaporator core having one or more coil fins to cool and dehumidify moisture-containing air caused to flow through the HVAC system and into a passenger compartment, the evaporator housing including air-contacting surfaces upon which water is to condense after the moisture-containing air flows thereover and is cooled and dehumidified;
 an air-communicating conduit operatively connected to, and downstream of, the evaporator core;
 a sump assembly including a side wall, a sump drain, and a sump pan having, an inner surface, the sump pan in fluid communication with the evaporator core, the sump assembly to receive water output of the evaporator core;
an exterior drain assembly operatively connected to the sump assembly; and
an ultra-violet-C (UV-C) light source positioned on an interior surface of the evaporator housing proximate the evaporator core and, in operation of the system, illuminates one or more coil fin surfaces, the air-communicating conduit downstream of the evaporator housing, and the sump assembly;
wherein at least a portion of the coil fin surfaces, the air-communicating conduit, or the sump assembly are indirectly illuminated by the UV-C light source; and
wherein the UV-C light source is arranged to, in operation of the system, deliver ultraviolet light to the coil fin surfaces, the air-communicating conduit, or the sump assembly by way of a light-affecting medium selected from a group consisting of water, a prism, a light-transporting fiber and tube.

2. The automotive HVAC system of claim 1, wherein:
the UV-C light source is a first UV-C light source;
the evaporator core comprises an upstream surface and a downstream surface; and
the HVAC system comprises a second UV-C light source including multiple light emitting diodes (LEDs) arranged to illuminate the upstream surface and the downstream surface of the evaporator core.

3. The automotive HVAC system of claim 1 wherein the UV-C light source has a peak emission between about 250 and about 280 nm.

4. The automotive HVAC system of claim 1 wherein the UV-C light source includes an ultraviolet light emitting diode (LED) or a high-power ultraviolet (HPUV) LED.

5. The automotive HVAC system of claim 1 wherein the UV-C light source is contained in a star base chip, chip on board, flip chip, multi-chip, strip set, printed circuit board, photonic lattice chip, or transistor case package.

6. The automotive HVAC system of claim 1 wherein the UV-C light source is mounted onto a heat sink, in a form of a passive heat exchanger, for adequate heat dissipation into a medium in contact with the heat sink.

7. The automotive HVAC system of claim 1 wherein a plurality of UV-C light sources are arranged in an array, lattice, and/or random pattern.

8. The automotive HVAC system of claim 1 further comprising a control device that, in operation of the HVAC system, controls the UV-C light source selectively to output the ultraviolet light at different wavelengths.

9. The automotive HVAC system of claim 1 comprising at least one other antimicrobial technology.

10. The automotive HVAC system of claim 1 further including a lockout sub-system, comprising a switch, to prevent skin contact.

11. The automotive HVAC system of claim 1 further comprising a control device that, in operation of the HVAC system, controls the UV-C light source selectively to output the ultraviolet light at different wattages.

12. An automotive heating, ventilation and air conditioning (HVAC) system, comprising:
an air-communicating conduit operatively connected to, and downstream of, an evaporator housing;
a sump assembly including a side wall, a sump drain, and a sump pan having an inner surface, the sump pan in fluid communication with an evaporator core having one or more coil fins, the sump assembly to receive water output of the evaporator core;
an exterior drain assembly operatively connected to the sump assembly;
an ultra-violet-C (UV-C) light source positioned on an interior surface of the evaporator housing proximate the evaporator core and, in operation of the system, illuminates one or more coil fin surfaces, the air-communicating conduit downstream of the evaporator housing, and the sump assembly; and
a control device configured that, in operation of the HVAC system, controls the UV-C light source selectively to output ultraviolet light at one or both of:
different wavelengths; and
different wattages;
wherein at least a portion of the coil fin surfaces, the air-communicating conduit, or the sump assembly are indirectly illuminated by the UV-C light source; and
wherein the UV-C light source is arranged to, in operation of the system, deliver ultraviolet light to the coil fin surfaces, the air-communicating conduit, or the sump assembly by way of a light-affecting medium selected from a group consisting of water, a prism, a light-transporting fiber and tube.

13. The automotive HVAC system of claim 12 further including a lockout sub-system, comprising a switch, to prevent skin contact.

14. The automotive HVAC system of claim 12, wherein:
the UV-C light source is a first UV-C light source;
the evaporator core includes air-contacting surfaces upon which water is to condense after moisture-containing air flows thereover and is cooled and dehumidified;
the air-contacting surfaces of the evaporator core comprise an upstream surface and a downstream surface; and
the HVAC system comprises a second UV-C light source including multiple light emitting diodes (LEDs) arranged to illuminate the upstream surface and the downstream surface of the evaporator core.

15. The automotive HVAC system of claim 12 comprising at least one other antimicrobial technology.

16. An automotive heating, ventilation and air conditioning (HVAC) system, comprising:
an air-communicating conduit operatively connected to, and downstream of, an evaporator housing;
a sump assembly including a side wall, a sump drain, and a sump pan having an inner surface, the sump pan in fluid communication with an evaporator core having one or more coil fins, the sump assembly to receive water output of the evaporator core;
an exterior drain assembly operatively connected to the sump assembly; and
an ultra-violet-C (UV-C) light source positioned on an interior surface of the evaporator housing proximate the evaporator core and, in operation of the system, illuminates one or more coil fin surfaces, the air-communicating conduit downstream of the evaporator housing, and the sump assembly; and
wherein at least a portion of the coil fin surfaces, the air-communicating conduit, or the sump assembly are indirectly illuminated by the UV-C light source; and
wherein the UV-C light source is arranged to, in operation of the system, deliver ultraviolet light to the coil fin surfaces, the air-communicating conduit, or the sump assembly by way of a light-affecting medium selected from a group consisting of water, a prism, a light-transporting fiber and tube.

17. The HVAC system of claim 16 further comprising a control device that, in operation of the HVAC system, controls the UV-C light source selectively to output the ultraviolet light at different wavelengths.

18. The HVAC system of claim 16 further comprising a control device that, in operation of the HVAC system, controls the UV-C light source selectively to output the ultraviolet light at different wattages.

19. The HVAC system of claim 16 further including a lockout sub-system to prevent skin contact.

\* \* \* \* \*